(12) United States Patent
Lluch

(10) Patent No.: US 7,238,022 B2
(45) Date of Patent: *Jul. 3, 2007

(54) AUXILIARY ELEMENTS FOR THE SEGMENTED DISTALISATION OF THE POSTERIOR JAWBONE SECTOR FROM CANINE TO MOLAR IN ORTHODONTIC TREATMENT

(76) Inventor: Luis Carriere Lluch, Calle/San Pedro Claver, 22, E-08017 Barcelona (ES)

( * ) Notice: Subject to any disclaimer, the term of this patent is extended or adjusted under 35 U.S.C. 154(b) by 10 days.

This patent is subject to a terminal disclaimer.

(21) Appl. No.: 11/181,444

(22) Filed: Jul. 14, 2005

(65) Prior Publication Data

US 2005/0260533 A1  Nov. 24, 2005

Related U.S. Application Data

(63) Continuation of application No. 10/490,620, filed as application No. PCT/ES2002/000463 on Oct. 2, 2002, now Pat. No. 6,976,839.

(30) Foreign Application Priority Data

| Oct. 3, 2001 | (ES) | .................................... 0102210 |
| Oct. 1, 2002 | (ES) | .................................... 0202219 |

(51) Int. Cl.
*A61C 7/00*    (2006.01)

(52) U.S. Cl. ........................................................ 433/18

(58) Field of Classification Search .................... 433/7, 433/17, 18, 19, 23
See application file for complete search history.

(56) References Cited

U.S. PATENT DOCUMENTS

| 473,040 | A | * | 4/1892 | Wilder | ......................... 433/10 |
| 4,861,268 | A | * | 8/1989 | Garay et al. | ................. 433/229 |
| 5,829,975 | A | * | 11/1998 | Gold | ............................ 433/19 |
| 5,873,715 | A | * | 2/1999 | Liou | ............................. 433/18 |

* cited by examiner

*Primary Examiner*—Melba Bumgarner
(74) *Attorney, Agent, or Firm*—Michael A. O'Neil

(57) ABSTRACT

The element consists of two elements, a mesial segment composed of an anterior enlargement which with its inner base is fixed to the canine by means of adhesive and with its external portion facilitates retention of an elastic element, an arched extension in the shoulder, finished off by a ball-and-socket member at its end which is introduced into a receptacle located in the middle portion and outside of the distal segment by its base is joined by means of adhesive to the upper molar, that ball-and-socket member having a plurality of channels which facilitate its connection to a plurality of pivots in the lateral parts of the receptacle, the rotation between the two being limited by complementary projections provided in each segment, wherein the device can advantageously be produced from translucent or transparent materials.

10 Claims, 9 Drawing Sheets

AUXILIARY ELEMENTS FOR THE SEGMENTED DISTALISATION OF THE POSTERIOR JAWBONE SECTOR FROM CANINE TO MOLAR IN ORTHODONTIC TREATMENT

CROSS-REFERENCE TO RELATED APPLICATIONS

This application is a continuation application of application Ser. No. 10/490,620 filed Mar. 24, 2004, now U.S. Pat. No. 6,976,839 ; which is the United States national phase of PCT application number PCT/ES2002/000463 filed Oct. 2, 2002, which claims priority of Spain patent application number 0102210 filed Oct. 3, 2001, and Spain patent application number 0202219 filed Oct. 1, 2002, all of which are incorporated herein by reference for all purposes.

The present invention relates to an auxiliary element for the segmented distalisation of the posterior jawbone sector from canine to molar in orthodontic treatment which is to improve, both mechanically and aesthetically, the elements which, with this same function, are currently being used.

The use of auxiliary elements in orthodontic treatment to achieve segmented distalisation by the inverse anchorage method is already known in current practice from the book "El Anclaje Inverso y su Ecuación" ("Inverse Anchorage and its Equation"), which envisages leaving the premolars free by means of a modular section.

In current practice the modular section is a segment of rectangular wire which is anchored on an independent element cemented on the molar in the form of a small ring, called a strip, by the distal or posterior part, while the mesial or anterior part is anchored to a bracket cemented directly on the surface of the canine.

Said modular section is metallic and is constructed by the orthodontist in the clinic, being removable without having to move the posterior or distal strip or the anterior or mesial bracket.

The function of said modular section is to force the distalisation of the posterior sector of the molar to the canine by using elastic intermaxillary bones.

Given its characteristics of structural rigidity, it also necessitates, in an active manner, rotation of the upper molar on its palatal root.

The auxiliary element for the segmented distalisation of the posterior jawbone sector from canine to molar in orthodontic treatment which forms the basis of the present invention is formed by two parts, an anterior or mesial segment which has a blunt projection upwards and forwards, with a retaining function for the use of elastic strips cemented on the vestibular surface of the upper canine being adapted to the curved anatomy of this facet and running up to its distal part in an arched shoulder, but without contacting the vestibular facets of the premolars, until it reaches the vestibular facet of the molar of the same side, finishing in an articulated ball-and-socket member.

The second segment is that which is cemented on the vestibular facet of the upper molar and consists of a base with blunt curves with a receptacle in its middle and outer parts, intended to house the ball-and-socket member which constitutes the distal element of the mesial segment.

The multi-direction articular movement, although limited because of the distalisation and rotation of the upper molar on the palatal root, is produced by the effect of the intermaxillary elastic elements.

Fitting and assembly of the two parts of the sectional apparatus for the distalisation is done before cementing in the patient's mouth.

The fundamental advantage of the apparatus which is claimed, with respect to that currently known, lies in the design and in the type of production of the segmented distalisation in which the molar, already known in practice, is forced to rotate by means of the rotation of the activated rectangular arc and is anchored on its vestibular surface, in contrast to the sectional distalisation element, which constitutes the basis of the present invention in which rotation is produced by the exclusive action derived from the use of the elastic intermaxillary elements of class II.

On the other hand, the configuration of the claimed element facilitates its manufacture with materials which can include translucent or transparent materials which give it aesthetics totally distinctive to those elements currently used and represents an important psychological aid for people who use it.

A variation of the present invention relates to the type of interrelation between the end of the mesial segment and the distal segment, whose interrelation is achieved by means of a spherical ball-and-socket member and transverse cylindrical articulation bolt which can be fixed in the body of the distal segment, adjusting to an orifice of the ball-and-socket member and allowing rotation thereof, said interconnection being achieved, in another variation, by means of a transverse cylindrical bolt arranged in an orifice of polygonal shape, for example square, of the spherical ball-and-socket member part associated with the distal end of the mesial segment.

Said variation relates to a new embodiment of the expansion for fastening of the elastic element, which adopts a slim and relatively long structure with a curvature adapted to that of the retaining base of the mesial segment.

To facilitate explanation, a few pages of drawings accompany the present description, in which by way of illustrative but non-limiting example is shown one embodiment of an auxiliary element for the segmented distalisation of the posterior jawbone sector from canine to molar in orthodontic treatment according to the principles of the claims.

FIGS. 17, 18, 19 and 20 each show sectional details of the coupling of the ball-and-socket member of the mesial segment to the distal segment.

As may be deduced from the pages of drawings, numerals designating the parts of the element described hereinafter have been used in the description of the claimed auxiliary element for the segmented distalisation of the posterior jawbone sector from canine to molar in orthodontic treatment.

1. Mesial segment fitted to the canine by its anterior part and to the distal segment by its posterior part.
2. Distal segment fitted to the molar.
3. Retaining base of the mesial segment fitted to the canine by means of adhesive.
4. Retaining base of the distal segment fitted to the molar by means of adhesive.
5. Rotation limiting shoe for the distal segment.
6. Rotation limiting flange in contact with 8.
7. Ball-and-socket member constituting the posterior end of the mesial segment, moving inside the cavity 13 of the distal segment.
8. Limit of articular rotational movement between the two segments, complementary to 6.
9. Projecting pivot of the cavity 13 of the distal segment for introduction into the slot 10 of the mesial segment to limit rotation thereof on its respective shaft.
10. Mesial segment slot in which the pivot 9 is introduced.
11. Blunt projection located in the external part of the anterior end of the mesial segment, running upwards and forwards, the function of which is to allow fixing of an elastic element of class II.
12. Posterior part of the mesial segment in arched form and finishing in the ball-and-socket member 7.
13. Cavity located in the distal segment and in the interior of which the ball-and-socket member 7 is accommodated.

Figure 1:
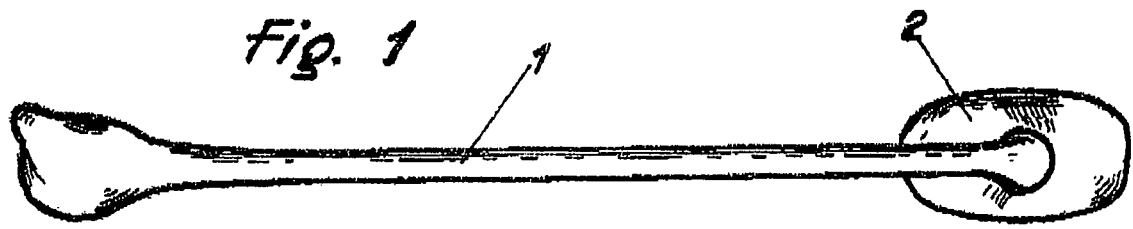
FIGS. 1, 2 and 3 are anterior and posterior plans and elevations of the claimed auxiliary element for the segmented distalisation of the posterior jawbone sector from canine to molar in orthodontic treatment.
Figure 2:
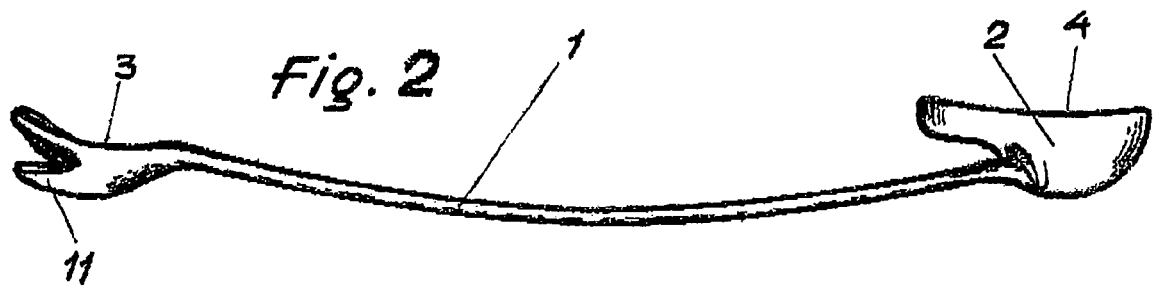
Figure 3:
Figure 4:
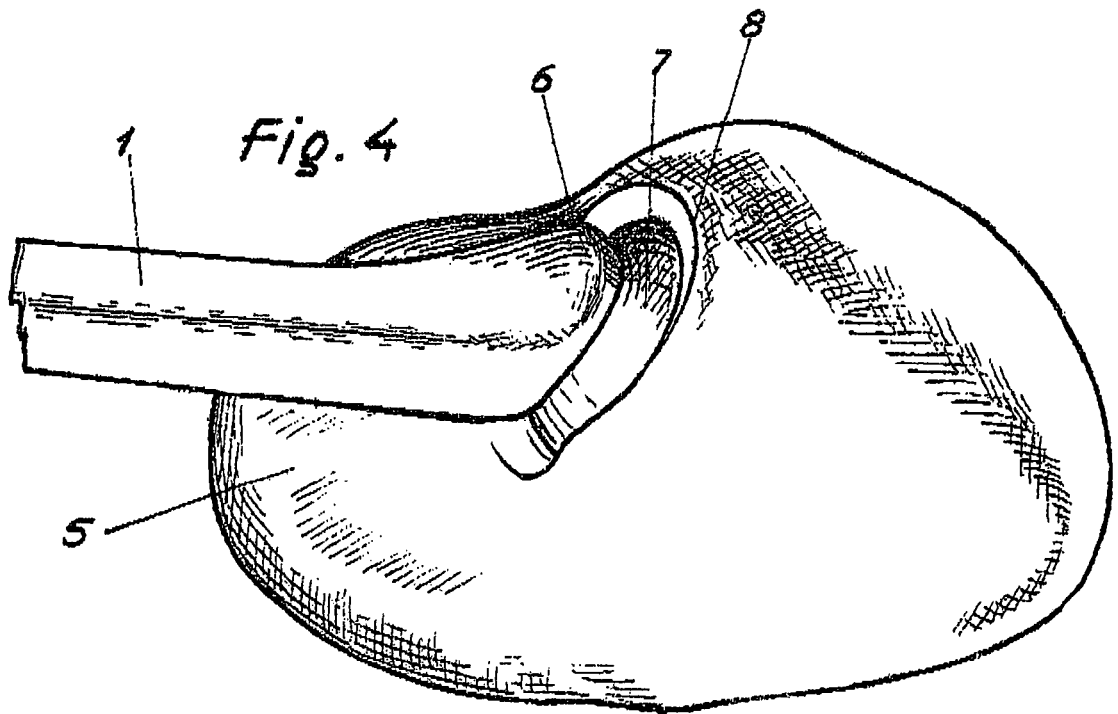
FIGS. 4 and 5 are respective plan views of the zone of connection of the two segments forming the claimed element.
Figure 5:
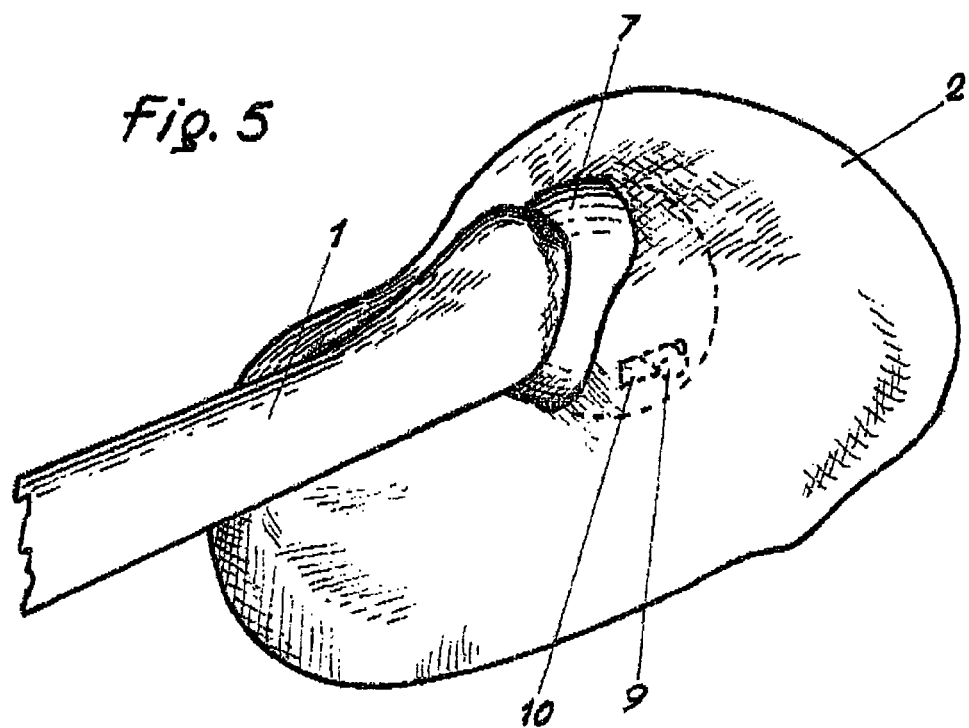
Figure 6:
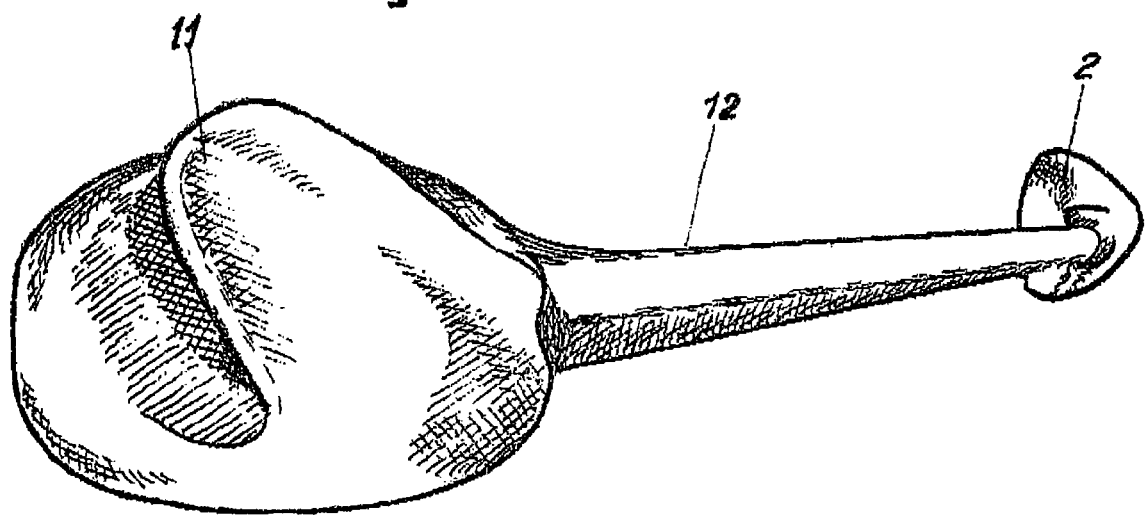
FIG. 6 is an anterior-posterior view of the assembly according to the present registration.
Figure 7:
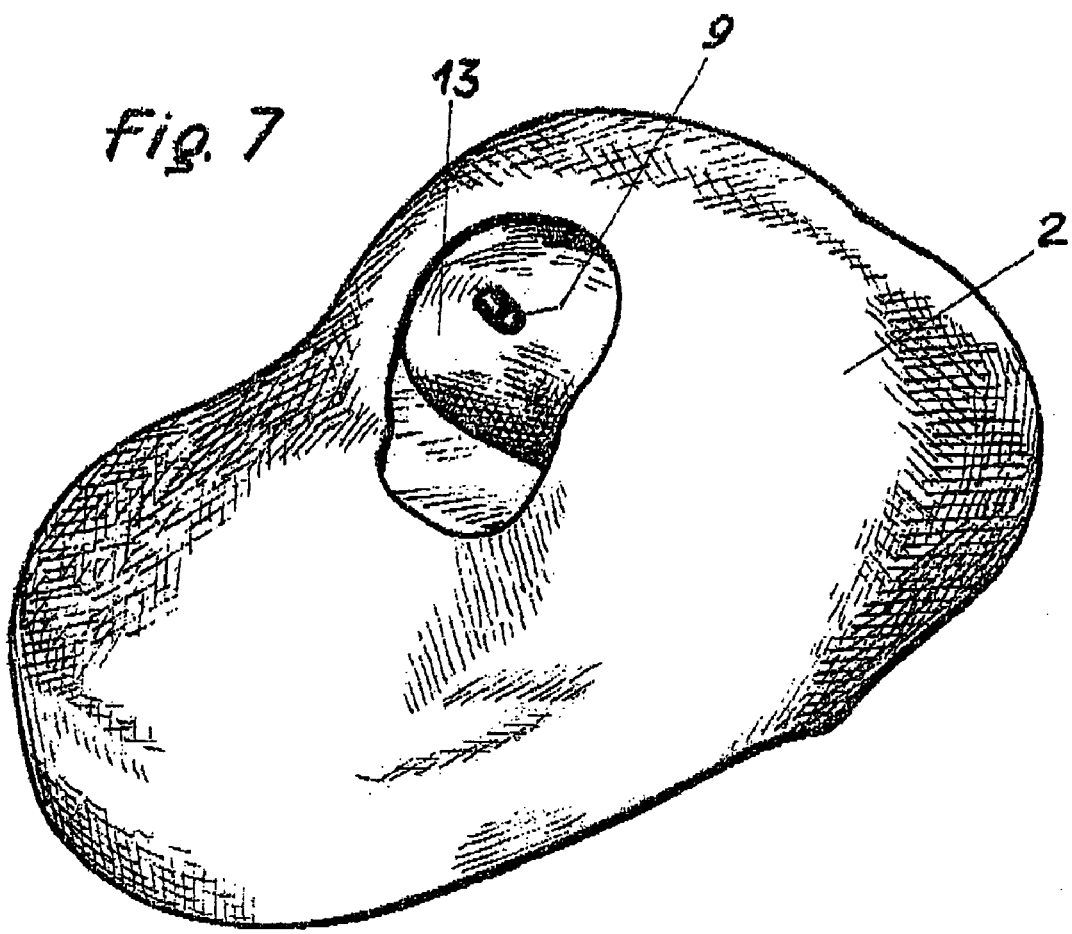
FIG. 7 is a plan view of the distal segment and FIG. 8 shows the posterior zone of the mesial segment.
Figure 8:
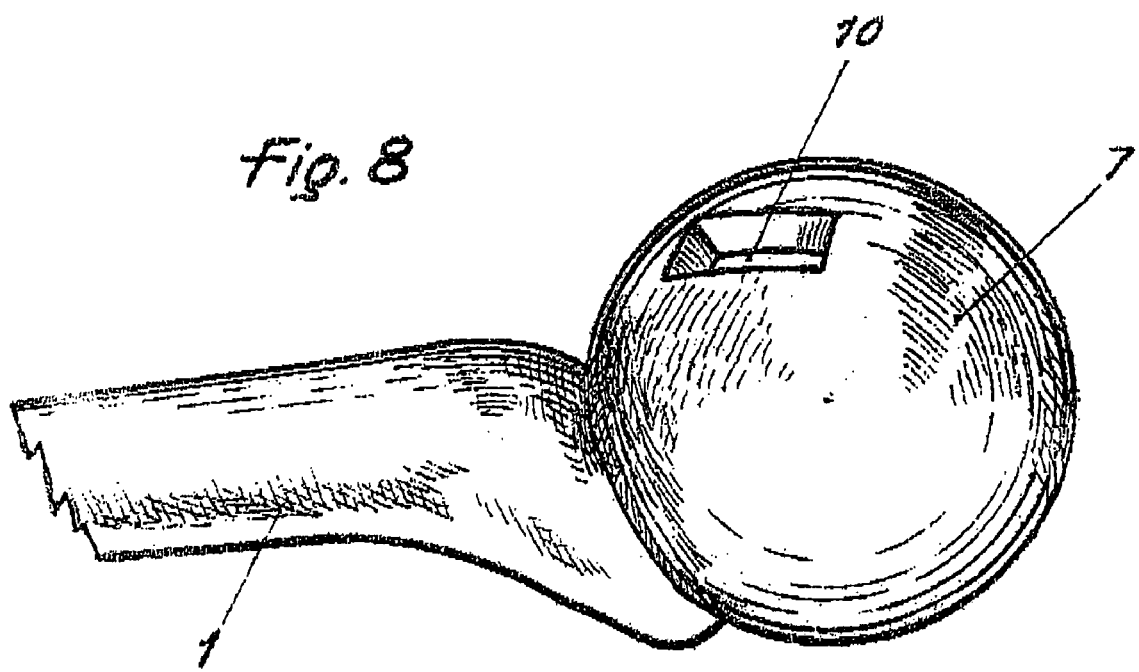
Figure 9:
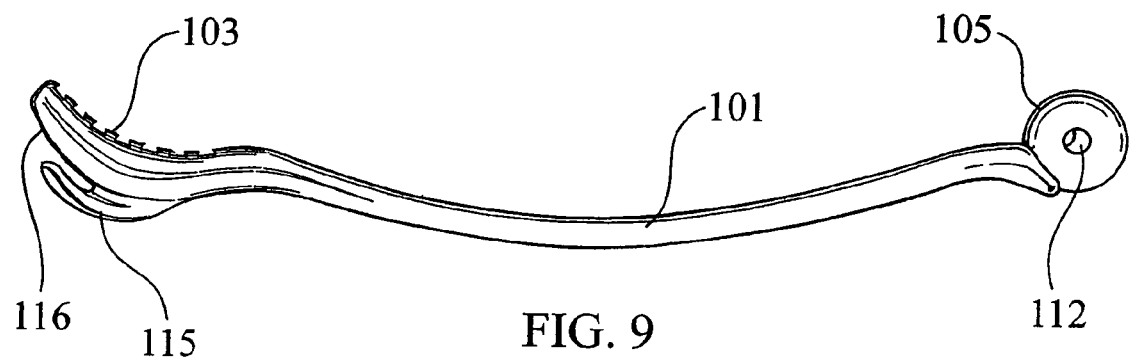
FIGS. 9 and 10 are perspective views of a mesial segment in accordance with the present improvements with respective variations of the housing orifice of the ball-and-socket shaft.
Figure 10:
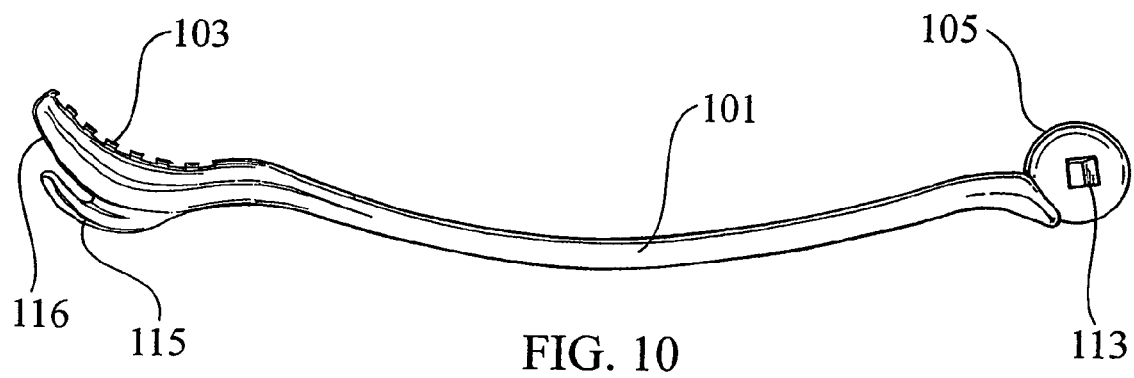
Figure 11:
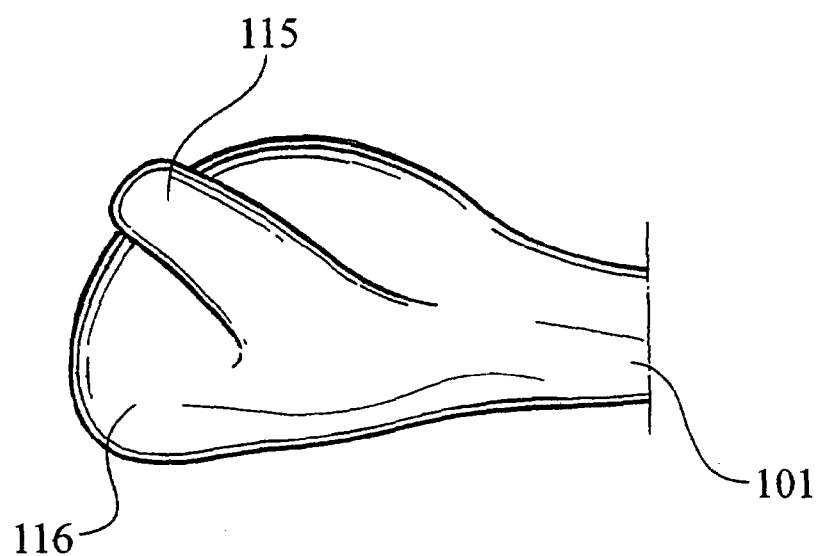
FIGS. 11, 12 and 13 show respective details of the expansion of the retaining base of the mesial segment.
Figure 12:
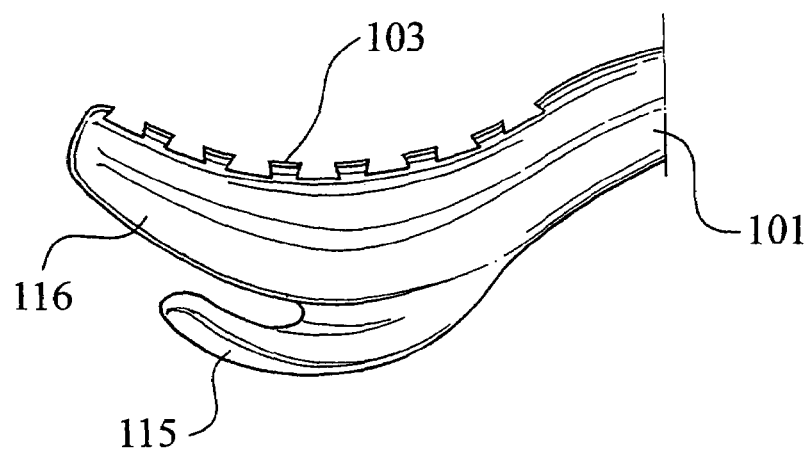
Figure 13:
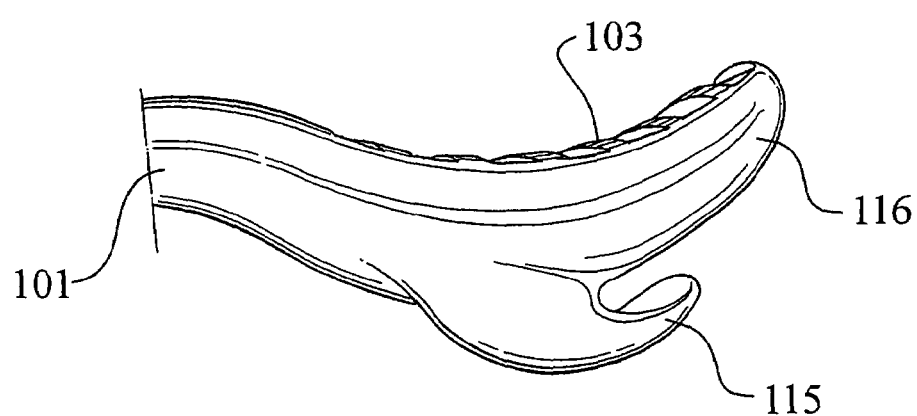
Figure 14:
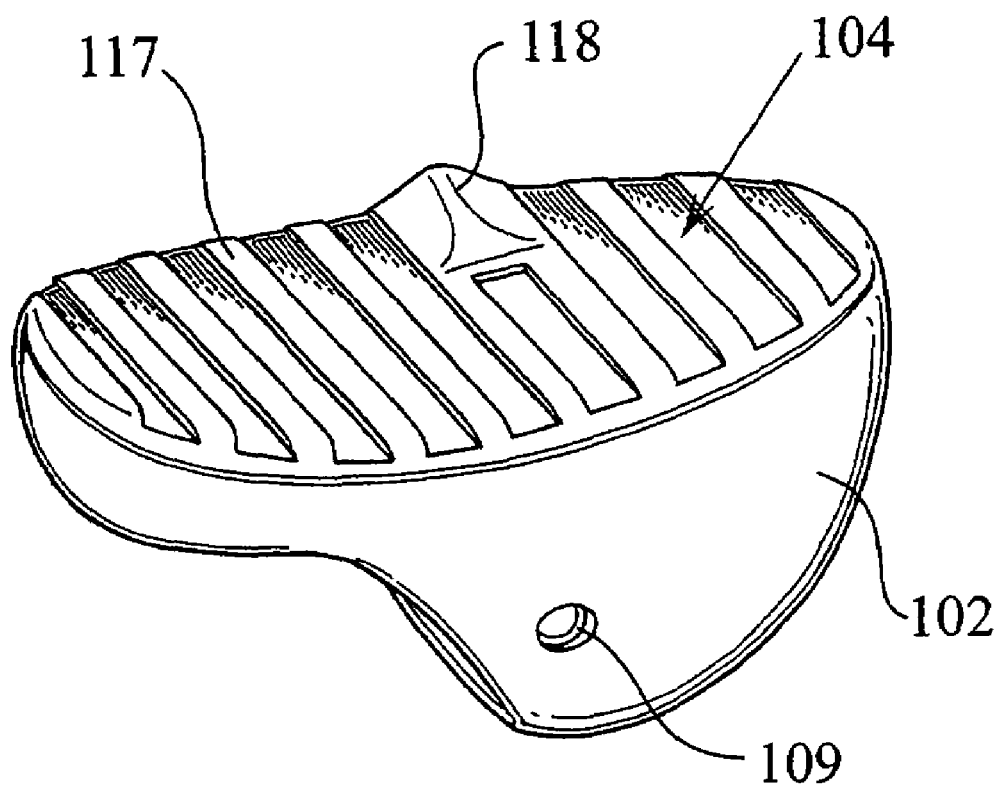
FIGS. 14 and 15 are respective perspective views of the distal segment.
Figure 15:
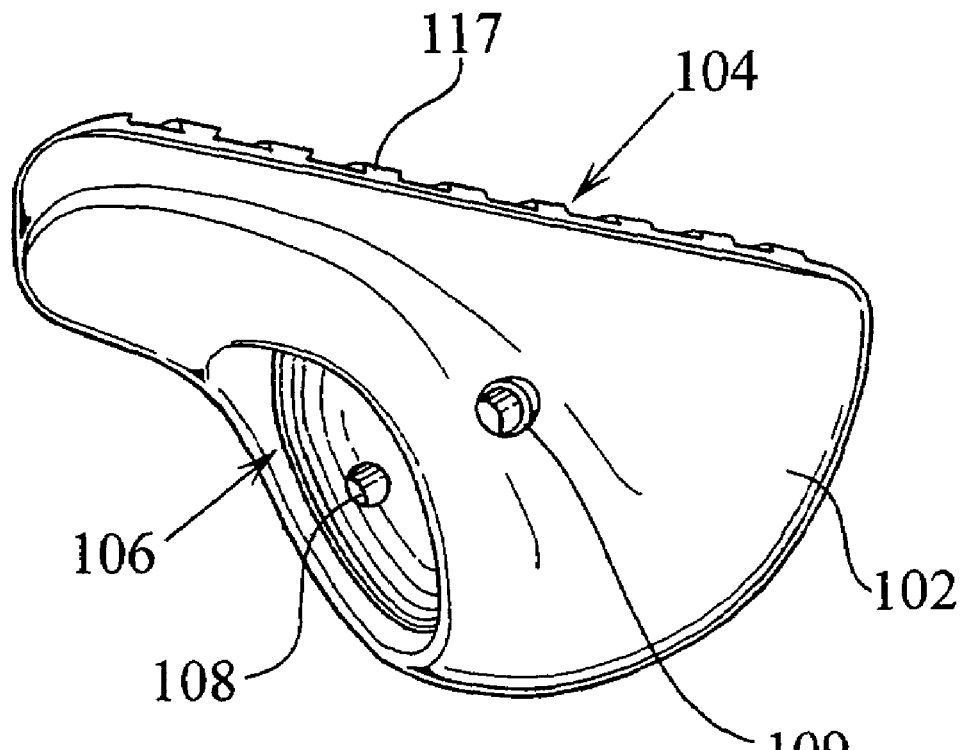
Figure 16:
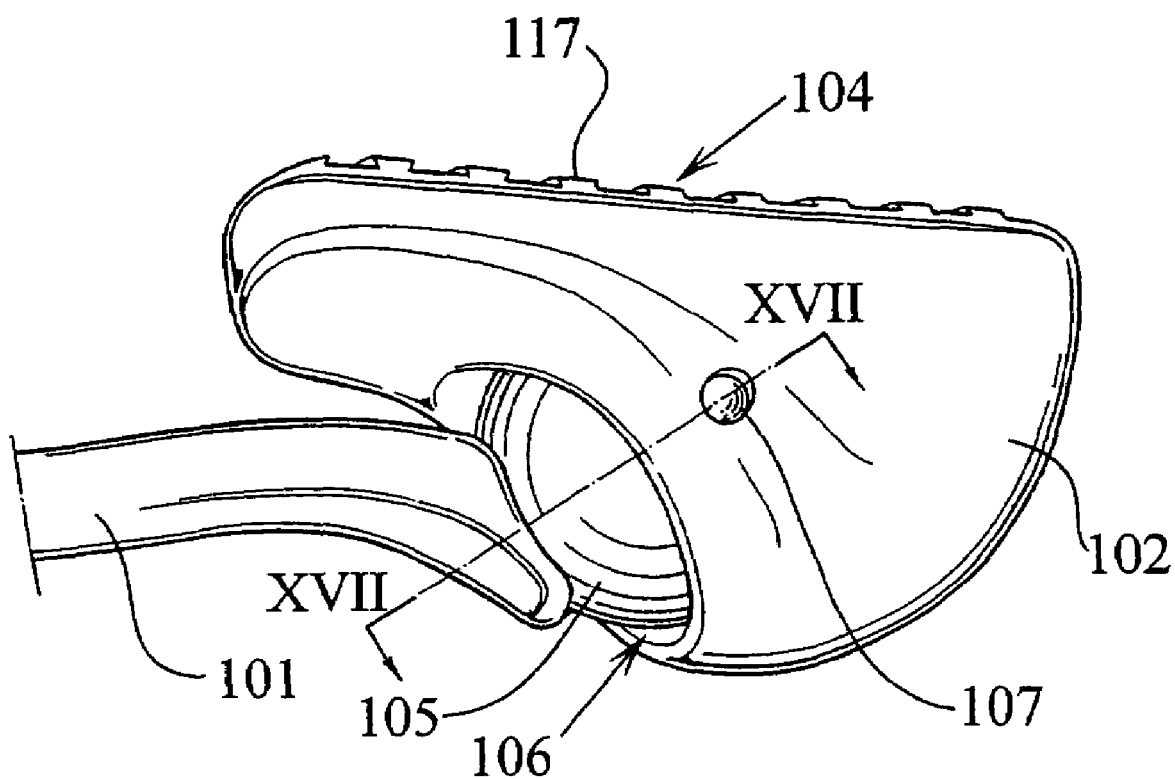
FIG. 16 is a perspective view of the coupling of the ball-and-socket member of the end of the mesial segment to the distal segment.
Figure 17:
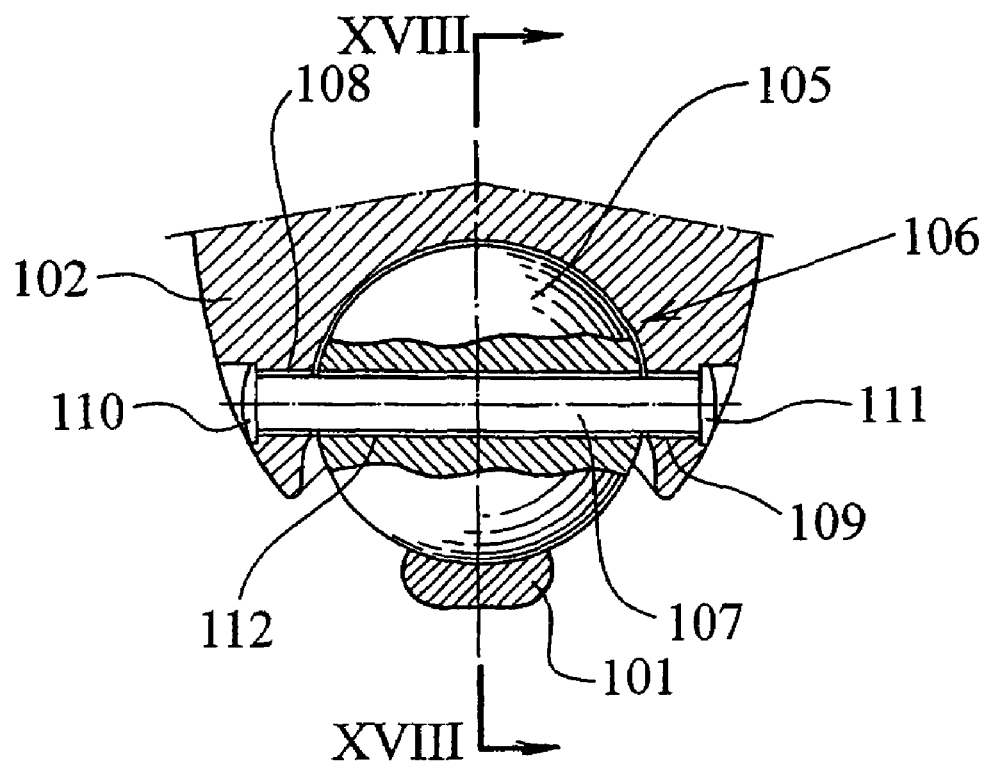
Figure 18:
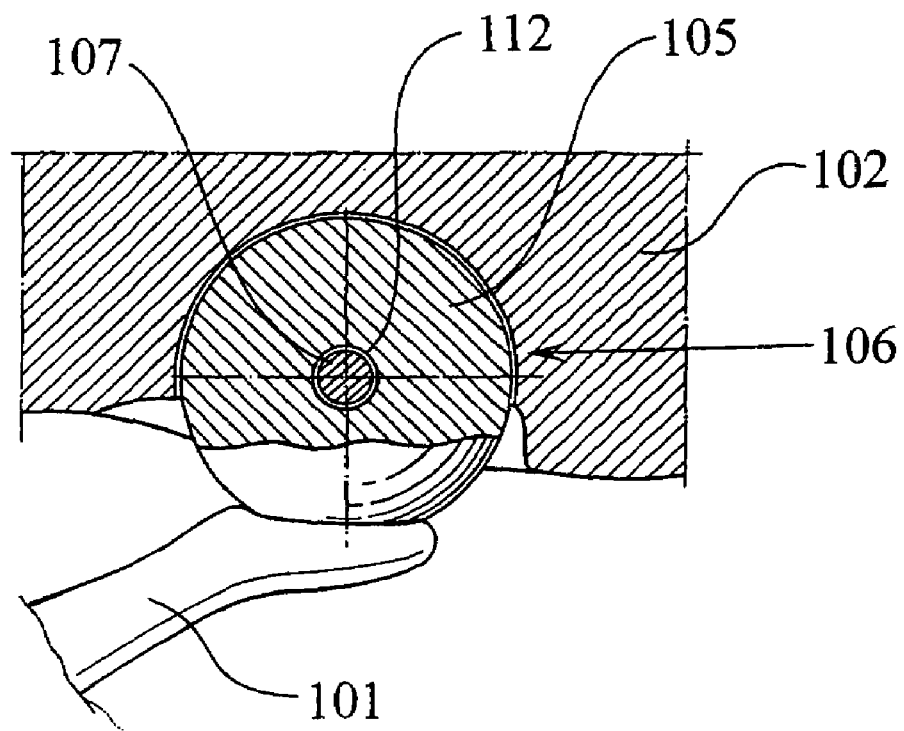

According to a variation of FIGS. 9 to 20, the present invention provides an articulation between the mesial segment 101 and the distal segment 102 with spherical terminals 105, so it fits in the interior of the mating housings 106 of the distal segment carrying the retaining base 104. The connection between the ball-and-socket member 105 and the coupling 106 is produced, as can be seen in FIG. 16 onwards, by introducing the spherical end 105 into the coupling 106 with transverse arrangement of a spud shaft 107, FIGS. 17 and 18, which crosses the distal segment 102 by means of aligned orifices 108 and 109 in which said shaft is fixed by various means, for example rivet heads 110 and 111 and other means, and said spud shaft 107 likewise passing through an orifice 112 of the body 105 of the ball-and-socket member, in which said shaft is rotatably housed. In this manner a very efficient arrangement of the ball-and-socket member is achieved between the end of the mesial segment and the distal segment.

Figure 19:
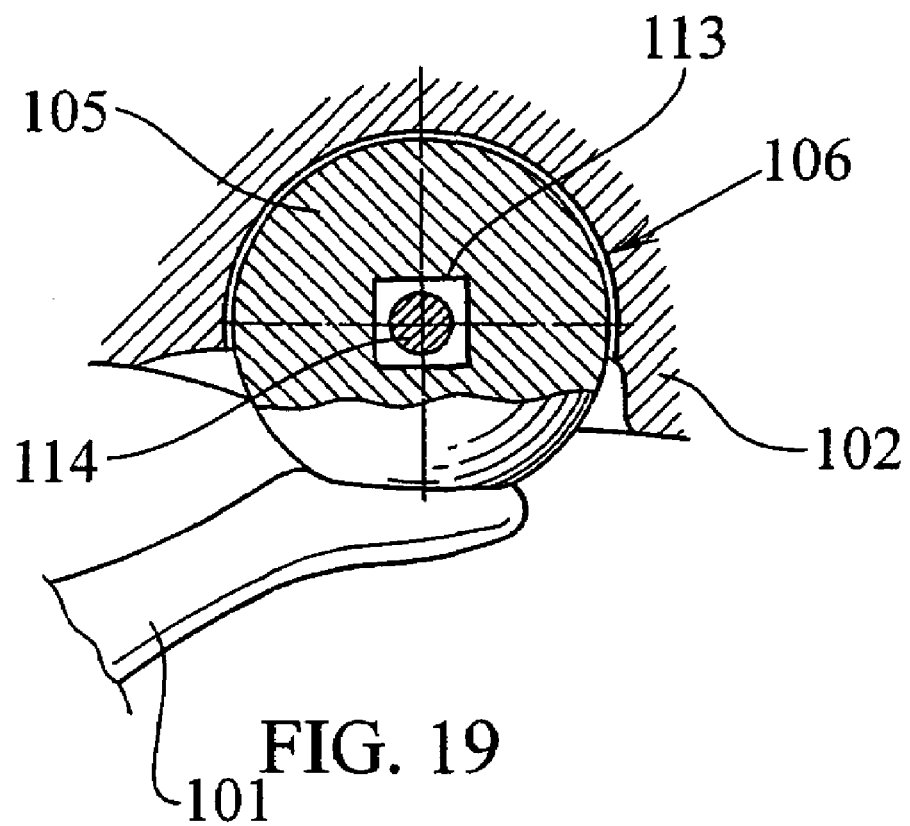
Figure 20:
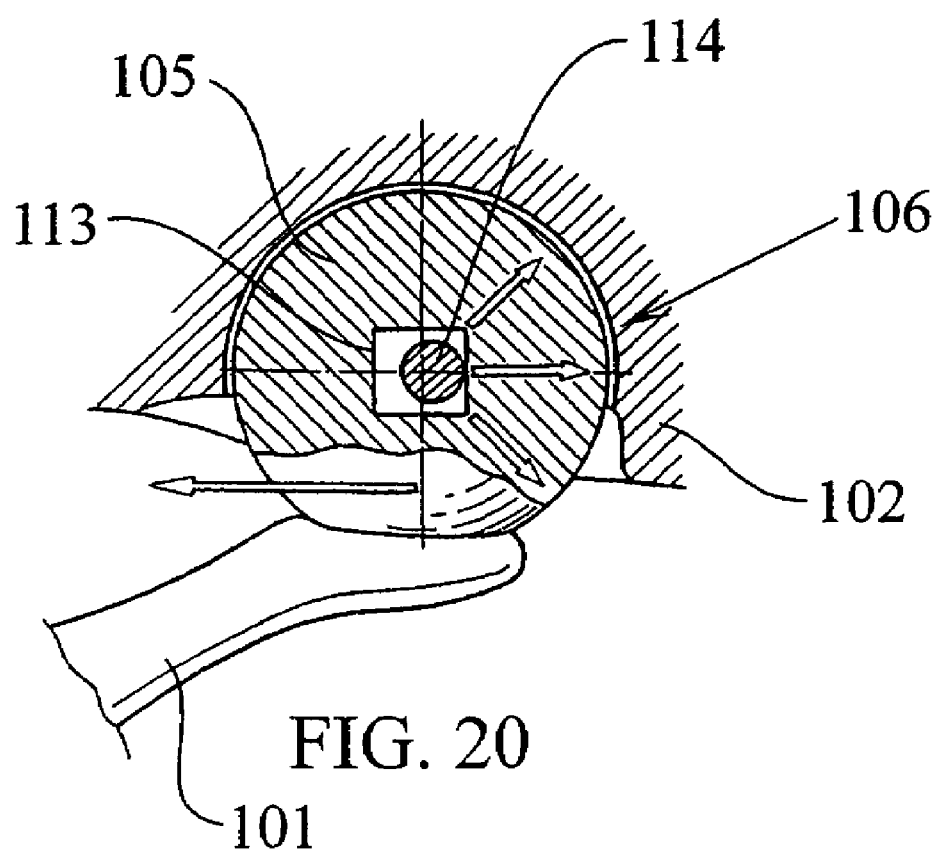

In addition to the version which has been shown in which the orifice of the spherical end of the ball-and-socket member 105 is circular, it is also possible to produce said orifice with a polygonal section, for example in the form of a square, as designated by the numeral 113 in FIGS. 19 and 20. In this case the retaining shaft 114 will equally be circular and have certain play with the walls of the polygonal orifice, allowing highly versatile coupling with the ball-and-socket member.

The variant which has been described likewise extends to the production of the expansion 115 for retention of the elastic means in the end enlargement 116 of the mesial segment carrying the retaining base 103 of said segment. Said expansion 115 has a slim structure and has a curvature like that of the respective expansion 115, as can be seen in the figures.

In accordance with the present invention the retaining base 104 of the distal segment 102 has, like the base 103 of the other end of the mesial segment, a finish adapted for better retention of the adhesive material, for example a plurality of straight transverse ridges 117 for better retention in the piece of tooth, likewise having an expansion 118 in the lateral part of the respective retaining base 104, for its adaptation to the vestibular facet of the molar.

Although the present invention is particularly intended for distal occlusions which include canines, premolars and molars, it can also be applied to segments including only molars and premolars and other dental parts.

Inspection of the drawings and understanding of the use of the elements constituting this application, identified by the aforementioned numerals, demonstrates the great simplicity of the claimed distalising element as well as the simplicity of its positioning and monitoring of its evolution in the mouth of a patient, in such a way as to combine the aesthetic advantage which can be achieved with translucent or transparent materials, all of which is evidence of the advance furnished by the claimed orthodontic device.

The invention claimed is:

1. For orthodontic treatment of a posterior jawbone sector extending from a canine tooth to a molar tooth on the same side of the jawbone, an orthodontic appliance comprising:
    a distal member having a retaining base for securing the distal member to the molar tooth;
    means for adhering the retaining base of the distal member to the molar tooth;
    a mesial member having an anterior end and a distal end;
    the anterior end of the mesial member including a retaining base for securing the mesial member to the canine tooth;
    means for adhering the retaining base of the mesial member to the canine tooth;
    the anterior end of the mesial member further including means for retaining an elastic element;
    means for pivotally connecting the distal end of the mesial member to the distal member; and
    means for limiting pivotal movement of the mesial member relative to the distal member.

2. The orthodontic appliance according to claim 1 wherein the means for pivotally connecting the distal end of the mesial member to the distal member includes a spherical terminal mounted at the distal end of the mesial member and a spherical cavity formed in the distal member for receiving the spherical terminal of the mesial member.

3. The orthodontic appliance according to claim 2 wherein the means for limiting pivotal movement of the mesial member relative to the distal member comprises:
    a projection extending inwardly from the distal member into the spherical cavity thereof;
    and a slot formed in the spherical terminal comprising the distal end of the mesial member; and
    the slot for receiving the projection of the distal member and thereby limiting pivotal movement of the mesial member relative to the distal member.

4. The orthodontic appliance according to claim 3 wherein the projection extending inwardly from the distal member into the spherical cavity thereof is formed integrally with the remainder of the distal member.

5. The orthodontic appliance according to claim 2 wherein the means for limiting pivotal movement of the mesial member relative to the distal member comprises:
    an orifice comprising the distal end of the mesial member extending transversely through the spherical terminal;

a pair of aligned orifices formed through the distal member on opposite sides of the spherical cavity formed therein; and a shaft extending through the aligned orifices formed in the distal member and the orifice extending through the spherical terminal comprising the distal end of the mesial member.

6. The orthodontic appliance according to claim 5 wherein the orifice comprising the distal end of the mesial member extending transversely through the spherical terminal is circular in cross section.

7. The orthodontic appliance according to claim 5 wherein the orifice comprising the distal end of the mesial member extending transversely through the spherical terminal is non-circular in cross section.

8. The orthodontic appliance according to claim 7 wherein the orifice comprising the distal end of the mesial member extending transversely through the spherical terminal is square in cross section.

9. The orthodontic appliance according to claim 5 wherein the means for retaining an elastic element comprises a blunt projection extending upward and forward to facilitate retention of an elastic element.

10. The orthodontic appliance according to claim 1 wherein the means for retaining an elastic member comprises a blunt projection extending upward and forward to facilitate retention of an elastic element.

* * * * *